(12) United States Patent
Goldman

(10) Patent No.: US 7,881,877 B2
(45) Date of Patent: Feb. 1, 2011

(54) TECHNIQUES FOR DETERMINING THE EFFECTS ON A SYSTEM OF A COMPONENT THAT HAS FOUR STATES

(75) Inventor: Lawrence Goldman, Baltimore, MD (US)

(73) Assignee: University of Maryland, Baltimore, Baltimore, MD (US)

( * ) Notice: Subject to any disclaimer, the term of this patent is extended or adjusted under 35 U.S.C. 154(b) by 840 days.

(21) Appl. No.: 11/687,635

(22) Filed: Mar. 17, 2007

(65) Prior Publication Data

US 2007/0288215 A1   Dec. 13, 2007

Related U.S. Application Data

(60) Provisional application No. 60/783,935, filed on Mar. 20, 2006.

(51) Int. Cl.
| | |
|---|---|
| G01N 33/48 | (2006.01) |
| G01N 31/00 | (2006.01) |
| G06G 7/48 | (2006.01) |
| G06G 7/58 | (2006.01) |
| C12N 9/00 | (2006.01) |

(52) U.S. Cl. .............................. 702/19; 702/22; 703/11; 703/12; 435/183

(58) Field of Classification Search ........................ None
See application file for complete search history.

(56) References Cited

PUBLICATIONS

Hoshino et al. Mechanism of intramolecular rearrangements of (Acetylacetonato)bis(4,4,4-trifluoro-1-phenyl-1,3-butanedionato)ruthenium(III). Inorganic Chemistry, 1990, vol. 29, pp. 4816-4820.*

Goldman L. Quantitative analysis of a fully generated four-state kinetic scheme. Biophysical Journal, vol. 91, Jul. 2006, pp. 173-178.*

Hodgkin et al. Currents carried by sodium and potassium ions through the membrane of the giant axon of Loligo. Journal of Physiology, 1952, vol. 116, pp. 449-472.*

Schmidt et al. Protein kinetics: structures of intermediates and reaction mechanism from time resolved x-ray data. PNAS, vol. 101, 2004, pp. 4799-4804.*

Blaustein, R.O, Kinetics of tethering quaternary ammonium compounds to K+ channels, J. Gen. Physiol, Aug. 1, 2002, pp. 203-216, vol. 120, Publisher: The Rockefeller University Press, Published in: New York/USA.

Jackson, M.B. , Inversion of Markov processes to determine rate constants from single-channel data, Biophys. J. , Sep. 1, 1997, pp. 1382-1394, vol. 73, Publisher: The Biophysical Society, Published in: Bethesda, MD/USA.

* cited by examiner

*Primary Examiner*—Russell S Negin
(74) *Attorney, Agent, or Firm*—Ditthavong Mori & Steiner, P.C.

(57) ABSTRACT

Techniques for determining effects on a biological system include determining rate constants for a particular time interval starting at an initial time. Each rate constant indicates a rate of transition from one of four states to a different one of the four states for a component of a biological system in presence of an external factor. A temporal change in a probability that the component is in a particular state after the initial time is determined without numerical iteration over multiple time steps. This includes determining three relaxation time constants that describe exponential changes based on the rate constants. The effect of the external factor on the biological system is determined based on the temporal change in the probability that the component is in the particular state. The probability at an arbitrary time is determined based on the rate constants and initial probabilities.

18 Claims, 5 Drawing Sheets

242
DETERMINE THREE EXPONENTIAL RELAXATION TIME CONSTANTS BASED ON RATE CONSTANTS

244
DETERMINE STEADY STATE PROBABILITY FOR PARTICULAR STATE BASED ON RATE CONSTANTS

250
DETERMINE INITIAL RATES OF TEMPORAL CHANGE FOR THREE STATES BASED ON THE RATE CONSTANTS AND THE INITIAL PROBABILITIES

252
DETERMINE INITIAL RATE OF TEMPORAL CURVATURE FOR PARTICULAR STATE BASED ON RATE CONSTANTS AND INITIAL RATES OF TEMPORAL CHANGE

260
DETERMINE PARTICULAR PROBABILITY AT TIME T
BASED ON TIME T;
THREE EXPONENTIAL RELAXATION TIMES;
STEADY STATE PROBABILITY FOR PARTICULAR STATE;
INITIAL PROBABILITY FOR PARTICULAR STATE
INITIAL RATE OF TEMPORAL CHANGE FOR PARTICULAR STATE; AND
INITIAL RATE OF TEMPORAL CURVATURE FOR PARTICULAR STATE.

US 7,881,877 B2

TECHNIQUES FOR DETERMINING THE EFFECTS ON A SYSTEM OF A COMPONENT THAT HAS FOUR STATES

CROSS-REFERENCE TO RELATED APPLICATIONS

This application claims benefit of Provisional Appln. 60/783,935, filed Mar. 20, 2006, the entire contents of which are hereby incorporated by reference as if fully set forth herein, under 35 U.S.C. §119(e).

STATEMENT OF GOVERNMENTAL INTEREST

This invention was made with Government support under Contract No. HL068733 awarded by the National Institutes of Health. The Government has certain rights in the invention.

BACKGROUND OF THE INVENTION

1. Field of the Invention

The present invention is directed to determining an effect of a factor on a biological system by determining a temporal change in probability of a component occupying a particular one of up to four distinguishable configurations, called states. In a particular embodiment, an effect of a factor (such as presence of a ligand or introduction of a voltage change) on an ion channel in a membrane of a cell is determined by determining a temporal change in probability that the ion channel is in one of four distinguishable states.

2. Description of the Related Art

Many biological systems important to a normal or diseased processes in a cell can be described as dependent on the population of different states of each of one or more different components, especially protein molecules. A protein molecule typically has many possible configurations, both absent external forcing and in response to the presence of external factors that exert some force on the protein. External factors can take many forms, from the application of an external voltage to the presence of ligands that bind at one or more sites on the protein. The probability that a protein is in one configuration or another is affected by these factors. The probability can be expressed by repeating an experiment many times with the same protein starting configuration and the introduction of the same factor and counting the occurrence of each state in the group of experiments. By the same token, the probability can be expressed by determining the percentage of a large number of the same protein that occupies each of the states. The bulk process of the cell is then dependent in part on the percentage of the population in each of the states.

For example, a protein that resides in a cell interior is acted upon by a therapeutic pharmacological agent when the protein is in one configuration, but not in a different configuration. The effectiveness of the therapeutic agent then depends on the probability that the protein is in a particular state, which corresponds to the population of the different states for a large number of molecules of that protein.

In one well known and heavily studied example, the protein molecule serves as a gated ion channel in a cell membrane that blocks passage of a certain ion in one or more states and allows passage of the certain ions through the membrane in one or more other states that can be induced by application of a certain voltage as an external gating factor. The controlled passage of such ions is essential in some very important bulk cell processes, such as the conduction of electrical impulses in nerve cells and muscle cells. The open state of an ion channel can be measured by a current that flows through the channel. When a channel is closed or inactive, no ions flow and current is zero. When an ion channel is inactive, it does not respond to the external gating factor by switching to an open state.

FIG. 1 is graph 100 that illustrates the measured responses of an ion channel to a voltage change. Graph 100 includes a trace 110 of voltage with time, eight individual traces 120a, 120b, 120c, 120d, 120e, 120f, 120g, 120h (collectively referenced herein as individual traces 120) of ion current with time for a single ion channel, and an average trace 130 of ion current with time for 40 consecutive single channel traces. FIG. 1 is from L. Goldman, "Stationarity of Sodium Channel Gating Kinetics in Excised Patches from Neuroblastoma N1E 115," *Biophysical Journal*, vol. 69, pp 2364 to 2368, December 1995 (hereinafter Goldman I), the entire contents of which are hereby incorporated by reference as if fully set forth herein. A horizontal axis scale 102 of graph 100 indicates an amount of time associated with the scale distance along a horizontal direction for trace 110 and traces 120 in graph 100. The length of scale 102 corresponds to 4 milliseconds (ms, 1 ms=$10^{-3}$ seconds). A horizontal axis scale 103 of graph 100 indicates an amount of time associated with the scale distance along a horizontal direction for trace 130. The length of scale 103 corresponds to 5 ms. The vertical change in voltage for trace 110 corresponds to a voltage step from −120 milliVolts (mV, 1 mV=$10^{-3}$ Volts) to −30 mV, which is held for 45 ms. A current is measured for a limited time after the voltage change in 7 traces (trace 120a, trace 120b, trace 120d, trace 120e, trace 120f, trace 120g, trace 120h) of the eight traces 120, as indicated by current in a negative direction through the membrane at trace portions 125a, 125b, 125d, 125e, 125e, 125f, 125g, corresponding to the 7 traces, respectively. Such a current indicates the single ion channel is in an open state. The current associated with an open state in traces 120 is indicated by the vertical scale 104 that indicates a current of 3 picoAmperes (pA, 1 pA=$10^{-12}$ Amperes). As can be seen from traces 120, the ion channel under study in FIG. 1 is more probably in the open state shortly after the voltage change, and then is more probably in a non-open state after about 20 ms. A more stable measurement of current is obtained by averaging over 40 such measurement to produce average trace 130. The current associated with average trace 130 is smaller than the individual measured currents, as indicated by the vertical scale 106 for trace 130, which corresponds to only 0.4 pA.

The features of average trace 130 include an exponentially increasing current in a negative direction along portion 131, and an exponentially decreasing current in the negative direction along portions 132 and 133. The response of such proteins to the presence or absence of external forcing is the object of efforts to predict and control cell processes, for both diagnosis and treatment of disease. Example uses include drug response and drug screening applications. The features of average trace 130 not only represent measured current changes but also indicate the temporal change in the probability that the ion channel is in the open state of the three or four states used to explain the membrane behavior. Viewed in this light, FIG. 1 shows an exponentially increasing probability of an open state along portion 131, and an exponentially decreasing probability of the open state along portions 132 and 133.

Observations of the type depicted in FIG. 1 have been explained by proposing three states for the protein serving as the ion channel. Other observations showing a delay in response to a voltage change have been explained using four or more states, including two or more closed or inactivation states (e.g., see R. Hahin and L. Goldman, "Initial Conditions and the Kinetics of the Sodium Conductance in Myxicola Giant Axons, I. Effects on the Time-Course of the Sodium Conductance," *Journal of General Physiology*, v72, pp 863-877, 1978; Goldman, "Gating current kinetics in Myxicola giant axons," *Biophysical Journal*, v59, pp 574-589, 1991; and L. Goldman, "Sodium Channel Inactivation from Closed States: Evidence for an Intrinsic Voltage Dependency," *Biophysical Journal*, v69, pp 2369-2377, 1995, the entire contents of each of which are hereby incorporated by reference as if fully set forth herein). Of course, each state used to explain an observable behavioral effect may consist of one or more actual states.

In many circumstances, the temporal changes of probability for states for a particular protein are predicted based on an initial population distribution among the states, values for rate constants for the transition from one state to another, and a system of ordinary differential equations. Generally, such rate constants can be assumed constant only for a particular protein and fixed external forcing. Nevertheless, much progress is made in predicting cell processes under these conditions. The solutions require numerical computations that are effectively performed only using computers, iterative methods, and long iteration times with many time steps.

The process is used both to determine rate constants that match observations in the presence of various factors, e.g., to fit the rate constants to the observations, and also to predict the behavior of the biological system based on the rate constants determined independently of those observations, e.g., based on previously determined rate constants in earlier experiments in the same laboratory or published in the scientific literature.

Analytical solutions that do not require computationally intense iterative methods have been developed for fewer than four states and for four states when certain rate constants are eliminated (forced to zero). However, with no general analytical solution, many workers are forced to employ the computationally intense iterative methods over many small time steps to deduce the temporal changes in probability for a particular state or states. This impedes both the determination of rate constants to match data and the prediction of effects of an external factor on a system, given its effect on one or more rate constants.

Based on the foregoing, there is a clear need for an analytical solution for time changes in probability for a general four state biological system based on rate constants alone or in combination with initial population distributions of the four states.

SUMMARY OF THE INVENTION

Techniques are provided for determining effects on a system of a component with four states. The techniques include determining rate constants for a particular time interval starting at an initial time. Each rate constant indicates a rate of transition from one of four states to a different one of the four states for a component of a biological system in presence of an external factor. A temporal change in a probability that the component is in a particular state after the initial time is determined without numerical iteration over multiple time steps. This includes determining three relaxation time constants that describe exponential changes based on the rate constants. The effect of the external factor on the biological system is determined based on the temporal change in the probability that the component is in the particular state.

In some embodiments initial probabilities for the four states are also determined. Then the probability at an arbitrary time is determined based on the rate constants and the initial probabilities.

These techniques allow temporal changes in behavior of system to be more quickly predicted. In turn, this allows predictions to be more easily compared to observations, and rate constants to be more quickly and easily tuned to observations.

BRIEF DESCRIPTION OF THE DRAWINGS

The present invention is illustrated by way of example, and not by way of limitation, in the figures of the accompanying drawings and in which like reference numerals refer to similar elements and in which.

DETAILED DESCRIPTION

Figure 1:
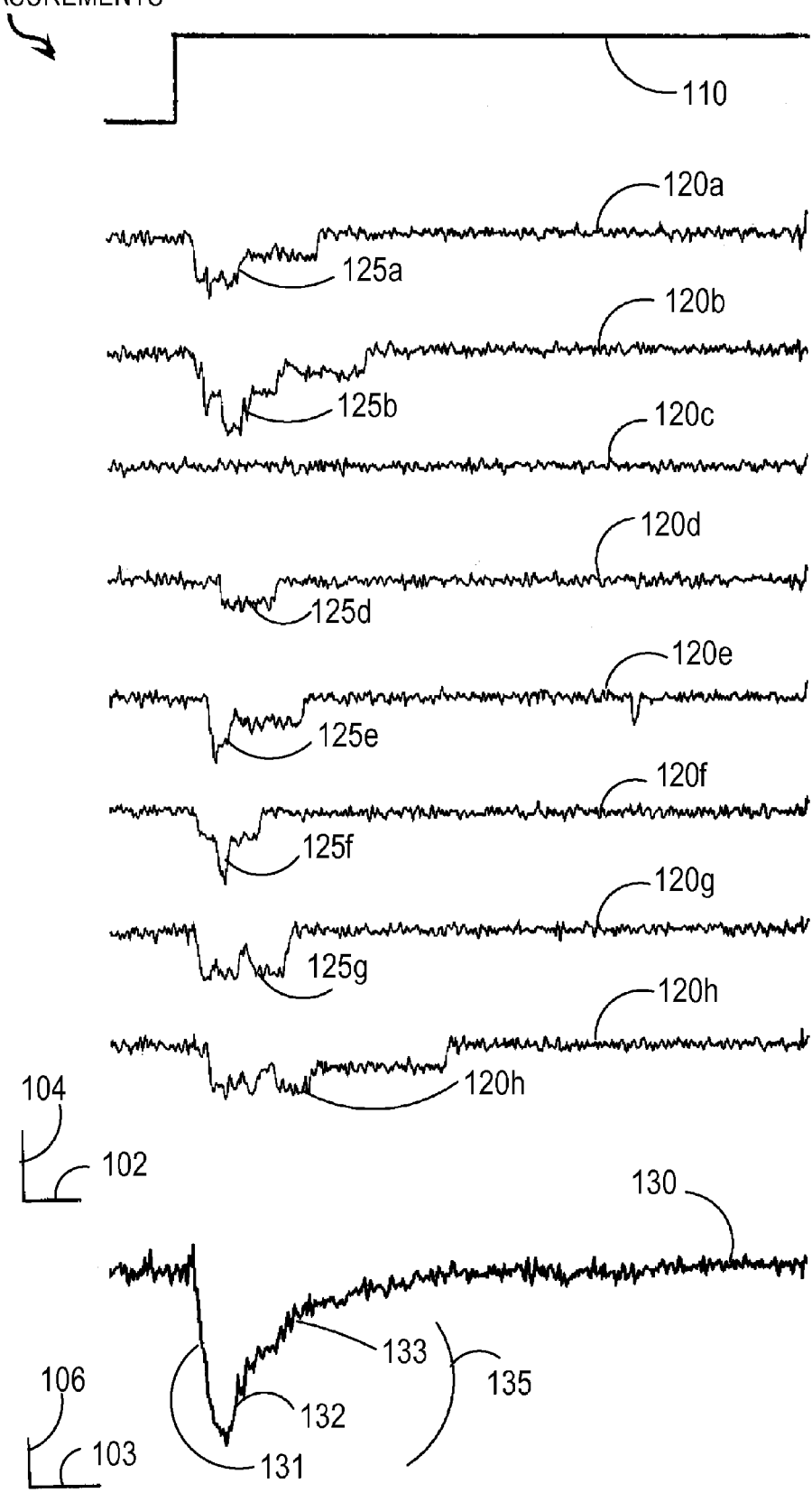
FIG. 1 is graph that illustrates the measured responses of an ion channel to a voltage change.

A method, computer-readable medium and apparatus are described for determining an effect of an external factor on a biological system. In the following description, for the purposes of explanation, numerous specific details are set forth in order to provide a thorough understanding of the present invention. It will be apparent, however, to one skilled in the art that the present invention may be practiced without these specific details. In other instances, well-known structures and devices are shown in block diagram form in order to avoid unnecessarily obscuring the present invention.

Some embodiments of the invention are described below in the context of an ion channel in a cell membrane in which the ion channel occupies one of an open state, a first closed state, a second close state corresponding to a delayed response to an external voltage, and an inactive state that does not open in response to an external voltage, but may recover to one of the closed states in response to an external voltage. One of these embodiments is described by L. Goldman, "Quantitative Analysis of a Fully Generalized Four State Genetic Scheme," *Biophysical Journal*, vol. 91, pp 173-178, July 2006 (hereinafter Goldman), the entire contents of which are hereby incorporated by reference as if fully set forth herein.

However, the invention is not limited to this context. In other embodiments, other biological systems, such as other cell organelles, are involved, having four or fewer states of proteins or other components of the biological system, that respond to other physical or chemical factors. For example, in some embodiments an ion channel in a cell membrane responds to a concentration of a ligand or other molecule in the vicinity of the ion channel. In some embodiments, the component is a protein that is not an ion channel for a cell membrane, and the external factor is a chemical compound of a class called a ligand, a receptor agonist, a receptor antagonist, an antibody, and a therapeutic agent. In still other embodiments, other non-biological systems, such as chemical, physical, climatic systems, are modeled with four states.

Furthermore, embodiments are described in the context of a forward analytical computation, starting with rate constants with or without initial probabilities and deducing temporal changes in probability, such as one or more relaxation time constants, of one or more states. However, in other embodiments, the reverse computation can also be performed analytically, without resort to numerical iterative methods, by making some simplifying assumptions. For example, given observed values of one or more relaxation time constants or steady state probabilities based on observed temporal changes, a corresponding number of unknown values of rate constants can be deduced by using algebra to invert one or more of the equations presented. Once inverted, the inverted equations can be used repeatedly, to deduce those rate constants from the relaxation times or steady state probabilities. Similarly, observations of probability amplitudes for one or more states at one or more times before steady state can be used to deduce a corresponding number of initial probabilities.

1. Overview

Figure 2:
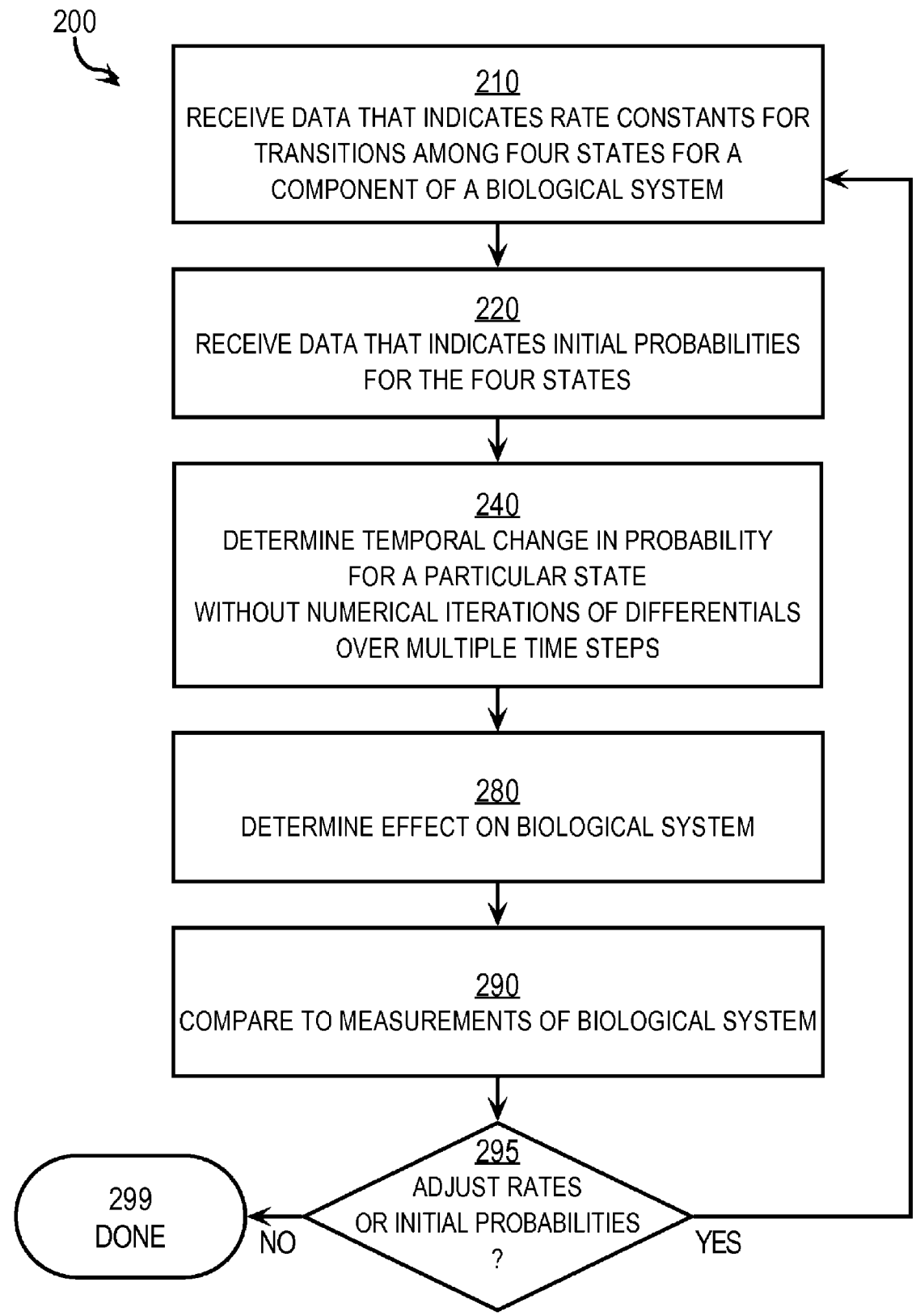
FIG. 2A is a flow diagram that illustrates at a high level a method for determining the effect on a biological system of a factor that affects any transition between two of four states of a component of that system, according to an embodiment.
FIG. 2B is a flow diagram that illustrates in more detail a step of the method of FIG. 2A, according to an embodiment.

FIG. 2A is a flow diagram that illustrates at a high level a method 200 for determining the effect on a biological system of a factor that affects any transition between two of four states of a component of that system, according to an embodiment. Although steps are shown in FIG. 2A and subsequent flow diagrams in a particular order for purposes of illustration, in other embodiments one or more steps may be performed in a different order or overlapping in time or may be omitted or changed in some combination of ways.

In step 210 data is received that indicates rate constants for transitions among four states for a component of a biological system. Any method known in the art for determining and receiving the rate constants data may be used. In some embodiments, the rate constants are entered manually or retrieved from a local or remote data base, or sent in response to a request sent to a different process on the same or different local or remote computer or received unsolicited from a process on the same or different local or remote computer. In some embodiments, the rate constants are based on values in published scientific literature. In some embodiments, rate constants are based on previous experiments. In some embodiments, one or more rate constants are based on estimated values refined based on output from a previous execution of the steps of method 200.

Figure 3:
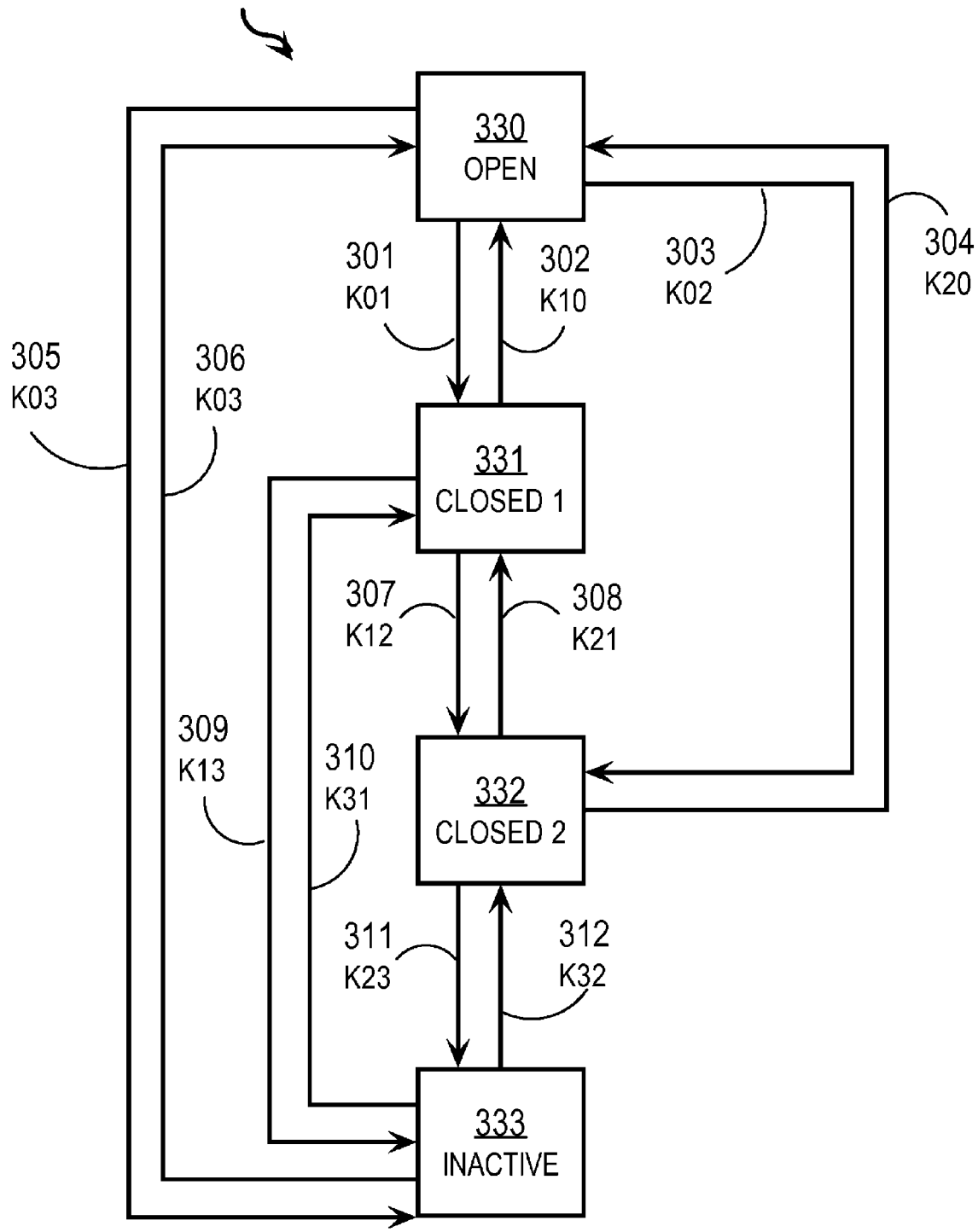
FIG. 3 is a block diagram that illustrates the four states and 12 associated rates for transitions between states, according to an example embodiment.

The four states for which rate constants are received are designated herein by the numerals 0, 1, 2, 3. A rate constant is designated by the letter k followed by two numerals, the first indicating the source state and the second indicating the destination state. There are twelve rate constants to be received during step 210 to encompass all transitions among the four states: k01, k10, k02, k20, k03, k30, k12, k21, k13, k31, k23, k32. FIG. 3 is a block diagram that illustrates the four states 331, 332, 333, 334 and 12 associated rates 301, 302, 303, 304, 305, 306, 307, 308, 309, 310, 311, 312 for transitions 300 between states, according to an example embodiment.

The rate constants received during step 210 apply in the presence of certain values for one or more external factors that affect the biological system that are introduced at a certain time, called the initial time. The rate constants are assumed constant so long as the external factor values are approximately constant.

In step 220, data is received that indicates initial probabilities for the four states. Any method known in the art for receiving the initial probability data may be used, as described above for rate constants data. A probability is designated herein by the letter P followed by a numeral that indicates the state. A probability of a state at the initial time is called the initial probability and is designated by the letter "i" following the numeral that indicates the state. There are up to four initial probabilities to be received during step 220 to encompass all four states: P0i, P1i, P2i, P3i. In some embodiments, the initial probabilities are determined based on the steady state probabilities computed in a previous execution of method 200 for different rate constants. The computation of steady state probabilities (designated: P0∞, P1∞, P2∞, P3∞ for states 0, 1, 2, 3, respectively, herein) are described in more detail below with reference to FIG. 2B. In some embodiments, in which only exponential relaxation times or steady state probabilities, or both, are determined, as described in more detail below with respect to FIG. 2B, step 220 is omitted.

In step 240, temporal changes in probability for one or more states are determined without numerical iterations of time differentials over multiple time steps. This direct determination without computationally intensive numerical iterations provides a distinct advantage for method 200 over prior art approaches when four states are involved. Step 240 is described in more detail below with reference to FIG. 2B.

In some embodiments, one or more of three relaxation time constants are determined for the change in probability of one or more states. The three relaxation time constants for state 0 are designated herein as "a," "b," "c." Three relaxation time constants are a characteristic of a four state system and can explain different exponential changes in probability with time in different portions of a trace (for example in portions 131, 132 and 133 of trace 130). Unlike prior approaches, the three relaxation time constants can be computed directly from rates, without numerical iteration and curve fitting. In some embodiments, one or more of four probabilities at one or more arbitrary times "t" are determined for the change in probability of corresponding one or more states. The four probabilities corresponding to the four states at time "t" are designated herein as "P0(t)," "P1(t)," "P2(t)" and "P3(t)," respectively. In some embodiments, step 240 includes presenting data that indicates the predicted change in probability of one or more states, e.g., a, b, c, P0∞, P1∞, P2∞, P3∞ or P0(t), or some combination.

In step 280, an effect on a biological system is determined based on the temporal change in probability. For example, a temporal change in average ion current is determined based on the temporal change in probability of an open state for an ion channel. In some embodiments, step 280 includes presenting data that indicates the predicted behavior of the biological system In step 290, the effect on the biological system is compared to measurements of the biological system. For example, a prediction of ion current determined in step 280 is compared to trace 130 in FIG. 1. In some embodiments, step 290 is omitted. For example, in drug screening or experimental planning, a variety of effects are determined in step 280 to determine which drug to test or experiment to perform before any measurements are obtained. In some embodiments, step 290 includes presenting data that indicates the relation of predicted and measured behavior of the biological system.

In step 295, it is determined whether to adjust rate constants or initial probabilities or both. For example, in embodiments in which the rate constants are not known precisely, initial guesses for one or more rate constants are used in step 210. Based on agreement with measurements in step 290, the rate constants are accepted or changed. Any method may be used to determine whether to adjust the rate constants and initial probabilities, and by how much. For example, optimal estimation techniques well known in the art may be used to determine a goodness of fit, and a change of goodness of fit with each change in one or more rate constants, and a next guess for one or more rate constants. In some embodiments, the changes in one or more rate constants are determined analytically by inverting one or more algebraic equations used during step 240 and making some simplifying assumptions, as appropriate. In some embodiments, step 295 is omitted and control passes directly to step 299 to terminate method 200.

If it is determined in step 295 to adjust one or more rate constants or initial probabilities, then control passes back to step 210 to receive data indicating the new rate constants, if any, and to step 220 to receive the new initial conditions, if any.

If it is determined in step 295 not to adjust one or more rate constants or initial probabilities, then control passes to step 299.

2. Example Embodiments

FIG. 2B is a flow diagram that illustrates in more detail step 240 of the method of FIG. 2A, according to embodiment 241. The steps of embodiment 241 are described below in detail for the four states of an ion channel, and are described in Goldman.

The four states for an ion channel are defined in Goldman as Open, Closed 1, Closed 2, and Inactive represented by the symbols O, 1, 2, IN, respectively. One of the closed 1 and closed 2 states represents a state in which there is a perceptibly longer delay between onset of a voltage change and an opening of an ion channel, the other closed state represents a closed state in which there is a shorter delay. For purposes of illustration, it is assumed that the ion channel states O, 1, 2, IN correspond to the general four states 0, 1, 2, 3, respectively. Furthermore, in Goldman, the rate constants are also designated by the letter k, but with the source and destination states expressed as subscripts following the letter k. The association between symbols used in Goldman and those used in the general case are listed in Table 1.

ating equations provided in Goldman. These constants are evaluated starting with Goldman equations 9 through 20 that define twelve combinations K1, K2, K3, K4, K5, K6, K7, K8, K9, K10, K11, K12 of the rate constants. Then Goldman equations 22 through 25 that define terms $\alpha$, $\beta$, $\gamma$, $\delta$ are evaluated. Then Goldman equations 43 and 44 that define terms A and B are evaluated. Then Goldman equations 41 and 42 that define terms $\theta$ and $\phi$ are evaluated. Then Goldman equations 38 through 40 that define relaxation constants a, b, c are evaluated. The relevant Goldman Equations are provided here as Equations 1 through 23.

$$K1 = k12 + k10 + k13 + k21 \tag{1}$$

$$K2 = k01 - k21 \tag{2}$$

$$K3 = k31 - k21 \tag{3}$$

$$K4 = k21 \tag{4}$$

$$K5 = k01 + k02 + k03 + k20 \tag{5}$$

$$K6 = k10 - k20 \tag{6}$$

$$K7 = k30 - k20 \tag{7}$$

$$K8 = k20 \tag{8}$$

$$K9 = k32 + k31 + k30 + k23 \tag{9}$$

$$K10 = k13 - k23 \tag{10}$$

$$K11 = k03 - k23 \tag{11}$$

$$K12 = k23 \tag{12}$$

$$\alpha = K1 + K5 + K9 \tag{13}$$

$$\beta = K1*K9 + K1*K5 + K5*K9 - (K2*K6 + K3*K10 + K7*K11) \tag{14}$$

TABLE 1

Mapping between symbols used herein and those used in Goldman.

| property | general symbol(s) | Symbol(s) in Goldman |
|---|---|---|
| states | 0, 1, 2, 3 | O, 1, 2, IN |
| rate constants (k) | k01, k10, . . . | $k_{O1}$, $k_{1O}$, . . . |
| Combinations of k | K1 through K12 | $K_1$ through $K_{12}$ |
| Probability of state 0 | P0 | Y |
| Probability of state 1 | P1 | X |
| Probability of state 2 | P2 | W |
| Probability of state 3 | P3 | Z |
| Initial Probability of states | P0i, P1i, P2i, P3i | Y(0), X(0), W(0), Z(0) |
| Initial rates of temporal change | P0i', P1i', P2i', P3i' | $\frac{d^2Y}{dt}(0), \frac{dX}{dt}(0), \frac{dW}{dt}(0), \frac{dZ}{dt}(0)$ |
| Initial rates of temporal curvature | P0i'', P1i'', P2i'', P3i'' | $\frac{d^2Y}{(dt)^2}(0), \frac{d^2X}{(dt)^2}(0), \frac{d^2W}{(dt)^2}(0), \frac{d^2Z}{(dt)^2}(0)$ |
| Steady state probabilities | P0∞, P1∞, P2∞, P3∞ | Y(∞), X(∞), W(∞), Z(∞) |

In step 242, three exponential relaxation time constants are determined based on the rate constants received in step 210, without numerical iteration over multiple time steps. For example, the relaxation time constants a, b, c for the Open state are computed based only on the rate constants by evalu- $$\gamma = K1*K5*K9 - (K1*K7*K11 + K2*K6*K9 + K2*K7*K10 + K3*K6*K11 + K3*K5*K10) \tag{15}$$

$$\delta = K3*K8*K10 - (K1*K7*K12 + K1*K8*K9 + K4*K7*K10 + K4*K6*K9 + K3*K6*K12) \tag{16}$$

$$A = \beta - (\alpha^2/3) \quad (17)$$

$$B = -1/27(2\alpha^3 - 9\alpha*\beta + 27\gamma) \quad (18)$$

$$\theta = \sqrt[3]{[-B/2 + \sqrt{(B^2/4 + A^3/27)}]} \quad (19)$$

$$\phi = \sqrt[3]{[-B/2 - \sqrt{(B^2/4 + A^3/27)}]} \quad (20)$$

$$a = \alpha/3 + (\theta + \phi) \quad (21)$$

$$b = \alpha/3 - [(\theta + \phi)/2 + ((\theta - \phi)/2)*\sqrt{(-3)}] \quad (22)$$

$$c = \alpha/3 - [(\theta + \phi)/2 - ((\theta - \phi)/2)*\sqrt{(-3)}] \quad (23)$$

These time constants can be used to describe the exponential changes in probability of a state over time using the mathematical constant base of the natural logarithm, designated "e," according to the form P0(t) is proportional to $e^{-at}$ or $e^{-bt}$ or $e^{-ct}$ or some combination, in at least a portion of a probability trace. In some embodiments, no more computations are made during step 240 and control returns to step 280 after step 242. In some of these embodiments, fewer than all three of Equations 21 through 23 are evaluated, to produce fewer than all three relaxation time constants a, b, c. In such embodiments, step 220 to receive the initial probabilities P0i, P1i, P2i, P3i, may be omitted.

An advantage of the analytical solution for relaxation time constants a, b, c is that an analytical equation relates a given relaxation time constant to a value of a particular rate constant or subset of rate constants. This is not directly known using the iterative numerical methods. With the iterative numerical methods, each kij value explored would require another P0 (t) simulation and then a time constants deduced by curve fitting each simulated trace. Often, just one or more simulated traces are presented to a user to assess visually—a tedious and error prone task. To determine whether other factors have affected the observations, additional iterative numerical simulations would have to be run. Third order differential equations would have to be derived and the relationship between the rate constants and α, β, γ would have to be defined.

In step 244 one or more steady state probabilities (designated "P0∞," "P1∞," "P2∞," "P3∞" for states 0 through 3, respectively) are determined for a corresponding one or more states, without numerical iteration over multiple time steps. The steady state probabilities are the probabilities at steady state when further temporal changes in probability are negligible. For example, the steady state probabilities P0∞, P1∞, P2∞, P3∞ are computed based only on the rate constants by further evaluating additional equations in Goldman, beyond those evaluated for step 242. These constants are evaluated with Goldman equations 27 through 31 (in which the steady state probabilities P0∞, P1∞, P2∞, P3∞ are represented by the symbols Y(∞), X(∞), W(∞), Z(∞), respectively, as listed in Table 1). In some embodiments fewer than all steady state probabilities are evaluated. For example, in some embodiments only P0∞ is evaluated using Equation 24. The relevant Goldman equations are provided here as Equations 24 through 27.

$$P0\infty = (K1*K7*K12 + K1*K8*K9 + K4*K7*K10 + K4*K6*K9 + K3*K6*K12 - K3*K8*K10)/\gamma \quad (24)$$

$$P1\infty = (K2*K7*K12 + K3*K5*K12 + K2*K8*K9 + K4*K5*k9 + K3*K8*K11 - K4*K7*K11)/\gamma \quad (25)$$

$$P3\infty = (k1*K8*K11 + K1*K5*K12 + K2*K8*K10 + K4*K5*K10 + K4*K6*K11 - K2*K6*K12)/\gamma \quad (26)$$

$$P2\infty = 1 - P0\infty - P1\infty - P3\infty \quad (27)$$

In some embodiments, no more computations are made during step 240 and control returns to step 280 after step 244. In such embodiments, step 220 to receive the initial probabilities P0i, P1i, P2i, P3i, may be omitted. Again, an advantage of the analytical solution for relaxation time constants steady state probabilities is that an analytical equation relates a given steady state probability to a value of a particular rate constant or subset of rate constants. This is not directly known using the iterative numerical methods.

In step 250 initial rates of temporal change for at least three of the four states (designated P0i', P1i', P2i', P3i' for states 0 through 3, respectively) are determined, without numerical iteration over multiple time steps. The initial rates of temporal change are the first time derivative of the probabilities at the initial time (t=0). For example, initial rates of temporal change P0i', P1i', P3i' are computed based on the rate constants and the initial probabilities P0i, P1i, P3i by further evaluating additional equations in Goldman, beyond those evaluated for step 242 and 244. These constants are evaluated with Goldman equations 6 through 8 at time t=0, substituting P0i, P1i, P3i for Y, X and Z, respectively. In embodiments that include step 250, step 220 to receive the initial probabilities P0i, P1i, P2i, P3i, should be included. The relevant Goldman equations are provided here as Equations 28 through 30.

$$P0i' = -K5*P0i + K6*P1i + K7*P3i + K8 \quad (28)$$

$$P1i' = -K1*P1i + K2*P0i + K3*P3i + K4 \quad (29)$$

$$P3i' = -K9*P3i + K10*P1i + K11*P0i + K12 \quad (30)$$

In step 252, initial rates of temporal curvature for at least one of the four states (designated P0i", P1i", P2i", P3i" for states 0 through 3, respectively) is determined, without numerical iteration over multiple time steps. The initial rates of temporal curvature are the second time derivative of the probabilities at the initial time (t=0). For example, initial rate of temporal curvature P0i" is computed based on the rate constants and the initial probabilities P0i, P1i, P3i by further evaluating additional equations in Goldman, beyond those evaluated for step 242, 244 and 250. These constants are evaluated with Goldman equation 37, substituting P0i", P0i', P1i', P3i' for $d^2Y/dt^2$, dY/dt, dX/dt and dZ/dt, respectively. In embodiment that include step 252, step 220 to receive the initial probabilities P0i, P1i, P2i, P3i, should be included. The relevant Goldman equation is provided here as Equations 31.

$$P0i'' = -K5*P0i' + K6*P1i' + K7*P3i' \quad (31)$$

In step 260 probability of one or more states at an arbitrary time t (designated P0(t), P1(t), P2(t), P3(t), for states 0 through 3, respectively) is determined, without numerical iteration over multiple time steps. For example, P0(t) is computed using the time t and the values determined above based on rate constants and the initial probabilities P0i, P1i, P3i by further evaluating an additional equation in Goldman, beyond those evaluated for step 242, 244, 250 and 252. P0(t) is computed with Goldman equation 36, substituting P0i", P0i', P0i, and P0∞ for $d^2Y/dt^2$, dY/dt, Y(0) and Y(∞), respectively. Goldman equation 36 is equivalent to the following Equations 32 to 35 for general states 0, 1, 2, 3:

$$Ca = [P0i'' + (b+c)*P0i' + b*c*(P0i - P0\infty)]/[(a-c)*(b-a)] \quad (32)$$

$$Cb = [P0i'' + (a+c)*P0i' + a*c*(P0i - P0\infty)]/[(c-b)*(b-a)] \quad (33)$$

$$Cc=[P0i''+(a+b)*P0i'+a*b*(P0i-P0\infty)]/[(c-b)*(a-c)] \tag{34}$$

$$P0(t)=P0\infty-Ca*e^{-at}-Cb*e^{-bt}-Cc*e^{-ct} \tag{35}$$

It is noted that for the duration of a time interval after the initial time during which the external factors are constant, the rate constants and the initial probabilities are also constant. As a result, the terms computed during steps 242 through 252 are also constant, i.e., do not vary with t over the time interval. That is the terms P0∞, Ca, Cb, Cc, a, b, c and e in the final equation are all constant. Thus steps 242 through 252 are executed once, then step 260 can be executed as many times as desired for a corresponding number of times t, in any order and with any large temporal separation. Such is not the case with prior art approaches that use numerical iterative techniques to advance the probabilities in small temporal increments.

3. Hardware Overview

Figure 4:
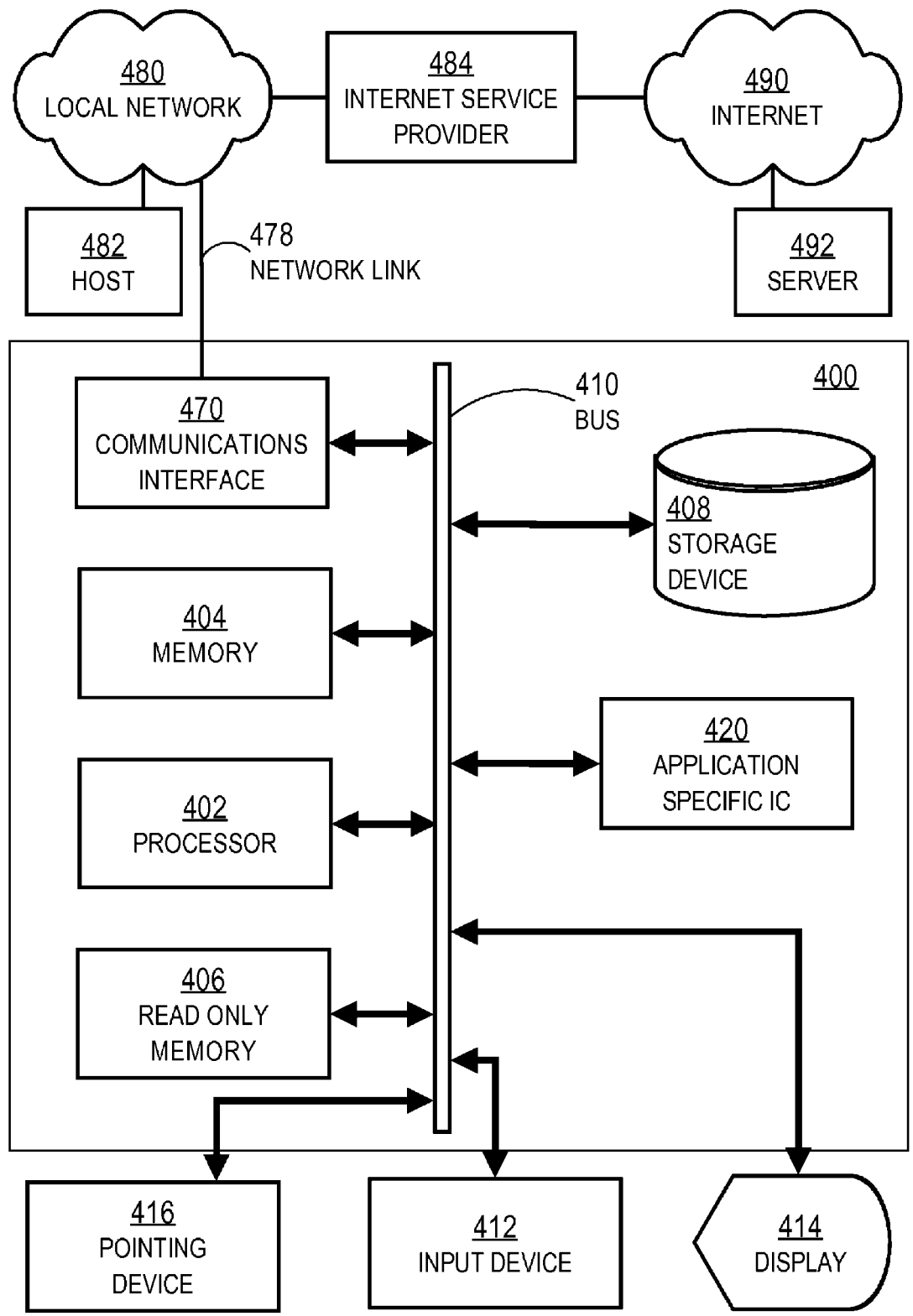
FIG. 4 is a block diagram that illustrates a computer system upon which an embodiment of the invention may be implemented.

FIG. 4 is a block diagram that illustrates a computer system 400 upon which an embodiment of the invention may be implemented. Computer system 400 includes a communication mechanism such as a bus 410 for passing information between other internal and external components of the computer system 400. Information is represented as physical signals of a measurable phenomenon, typically electric voltages, but including, in other embodiments, such phenomena as magnetic, electromagnetic, pressure, chemical, molecular atomic and quantum interactions. For example, north and south magnetic fields, or a zero and non-zero electric voltage, represent two states (0, 1) of a binary digit (bit). A sequence of binary digits constitutes digital data that is used to represent a number or code for a character. A bus 410 includes many parallel conductors of information so that information is transferred quickly among devices coupled to the bus 410. One or more processors 402 for processing information are coupled with the bus 410. A processor 402 performs a set of operations on information. The set of operations include bringing information in from the bus 410 and placing information on the bus 410. The set of operations also typically include comparing two or more units of information, shifting positions of units of information, and combining two or more units of information, such as by addition or multiplication. A sequence of operations to be executed by the processor 402 constitute computer instructions.

Computer system 400 also includes a memory 404 coupled to bus 410. The memory 404, such as a random access memory (RAM) or other dynamic storage device, stores information including computer instructions. Dynamic memory allows information stored therein to be changed by the computer system 400. RAM allows a unit of information stored at a location called a memory address to be stored and retrieved independently of information at neighboring addresses. The memory 404 is also used by the processor 402 to store temporary values during execution of computer instructions. The computer system 400 also includes a read only memory (ROM) 406 or other static storage device coupled to the bus 410 for storing static information, including instructions, that is not changed by the computer system 400. Also coupled to bus 410 is a non-volatile (persistent) storage device 408, such as a magnetic disk or optical disk, for storing information, including instructions, that persists even when the computer system 400 is turned off or otherwise loses power.

Information, including instructions, is provided to the bus 410 for use by the processor from an external input device 412, such as a keyboard containing alphanumeric keys operated by a human user, or a sensor. A sensor detects conditions in its vicinity and transforms those detections into signals compatible with the signals used to represent information in computer system 400. Other external devices coupled to bus 410, used primarily for interacting with humans, include a display device 414, such as a cathode ray tube (CRT) or a liquid crystal display (LCD), for presenting images, and a pointing device 416, such as a mouse or a trackball or cursor direction keys, for controlling a position of a small cursor image presented on the display 414 and issuing commands associated with graphical elements presented on the display 414.

In the illustrated embodiment, special purpose hardware, such as an application specific integrated circuit (IC) 420, is coupled to bus 410. The special purpose hardware is configured to perform operations not performed by processor 402 quickly enough for special purposes. Examples of application specific ICs include graphics accelerator cards for generating images for display 414, cryptographic boards for encrypting and decrypting messages sent over a network, speech recognition, and interfaces to special external devices, such as robotic arms and medical scanning equipment that repeatedly perform some complex sequence of operations that are more efficiently implemented in hardware.

Computer system 400 also includes one or more instances of a communications interface 470 coupled to bus 410. Communication interface 470 provides a two-way communication coupling to a variety of external devices that operate with their own processors, such as printers, scanners and external disks. In general the coupling is with a network link 478 that is connected to a local network 480 to which a variety of external devices with their own processors are connected. For example, communication interface 470 may be a parallel port or a serial port or a universal serial bus (USB) port on a personal computer. In some embodiments, communications interface 470 is an integrated services digital network (ISDN) card or a digital subscriber line (DSL) card or a telephone modem that provides an information communication connection to a corresponding type of telephone line. In some embodiments, a communication interface 470 is a cable modem that converts signals on bus 410 into signals for a communication connection over a coaxial cable or into optical signals for a communication connection over a fiber optic cable. As another example, communications interface 470 may be a local area network (LAN) card to provide a data communication connection to a compatible LAN, such as Ethernet. Wireless links may also be implemented. For wireless links, the communications interface 470 sends and receives electrical, acoustic or electromagnetic signals, including infrared and optical signals, that carry information streams, such as digital data. Such signals are examples of carrier waves.

The term computer-readable medium is used herein to refer to any medium that participates in providing information to processor 402, including instructions for execution. Such a medium may take many forms, including, but not limited to, non-volatile media, volatile media and transmission media. Non-volatile media include, for example, optical or magnetic disks, such as storage device 408. Volatile media include, for example, dynamic memory 404. Transmission media include, for example, coaxial cables, copper wire, fiber optic cables, and waves that travel through space without wires or cables, such as acoustic waves and electromagnetic waves, including radio, optical and infrared waves. Signals that are transmitted over transmission media are herein called carrier waves.

Common forms of computer-readable media include, for example, a floppy disk, a flexible disk, a hard disk, a magnetic tape, or any other magnetic medium, a compact disk ROM (CD-ROM), a digital video disk (DVD) or any other optical medium, punch cards, paper tape, or any other physical medium with patterns of holes, a RAM, a programmable ROM (PROM), an erasable PROM (EPROM), a FLASH-EPROM, or any other memory chip or cartridge, a carrier wave, or any other medium from which a computer can read.

Network link 478 typically provides information communication through one or more networks to other devices that use or process the information. For example, network link 478 may provide a connection through local network 480 to a host computer 482 or to equipment 484 operated by an Internet Service Provider (ISP). ISP equipment 484 in turn provides data communication services through the public, world-wide packet-switching communication network of networks now commonly referred to as the Internet 490. A computer called a server 492 connected to the Internet provides a service in response to information received over the Internet. For example, server 492 provides information representing video data for presentation at display 414.

The invention is related to the use of computer system 400 for implementing the techniques described herein. According to one embodiment of the invention, those techniques are performed by computer system 400 in response to processor 402 executing one or more sequences of one or more instructions contained in memory 404. Such instructions, also called software and program code, may be read into memory 404 from another computer-readable medium such as storage device 408. Execution of the sequences of instructions contained in memory 404 causes processor 402 to perform the method steps described herein. In alternative embodiments, hardware, such as application specific integrated circuit 420, may be used in place of or in combination with software to implement the invention. Thus, embodiments of the invention are not limited to any specific combination of hardware and software.

The signals transmitted over network link 478 and other networks through communications interface 470, which carry information to and from computer system 400, are exemplary forms of carrier waves. Computer system 400 can send and receive information, including program code, through the networks 480, 490 among others, through network link 478 and communications interface 470. In an example using the Internet 490, a server 492 transmits program code for a particular application, requested by a message sent from computer 400, through Internet 490, ISP equipment 484, local network 480 and communications interface 470. The received code may be executed by processor 402 as it is received, or may be stored in storage device 408 or other non-volatile storage for later execution, or both. In this manner, computer system 400 may obtain application program code in the form of a carrier wave.

Various forms of computer readable media may be involved in carrying one or more sequence of instructions or data or both to processor 402 for execution. For example, instructions and data may initially be carried on a magnetic disk of a remote computer such as host 482. The remote computer loads the instructions and data into its dynamic memory and sends the instructions and data over a telephone line using a modem. A modem local to the computer system 400 receives the instructions and data on a telephone line and uses an infra-red transmitter to convert the instructions and data to an infra-red signal, a carrier wave serving as the network link 478. An infrared detector serving as communications interface 470 receives the instructions and data carried in the infrared signal and places information representing the instructions and data onto bus 410. Bus 410 carries the information to memory 404 from which processor 402 retrieves and executes the instructions using some of the data sent with the instructions. The instructions and data received in memory 404 may optionally be stored on storage device 408, either before or after execution by the processor 402.

4. Extensions and Alternatives

In the foregoing specification, the invention has been described with reference to specific embodiments thereof. It will, however, be evident that various modifications and changes may be made thereto without departing from the broader spirit and scope of the invention. The specification and drawings are, accordingly, to be regarded in an illustrative rather than a restrictive sense.

What is claimed is:

1. A method for determining an effect of an external factor on a biological system by analyzing a given component of the biological system, wherein the given component occupies only one of four possible states, comprising the steps of:
   determining, for a particular time interval starting at an initial time, twelve non-degenerate and non-zero rate constants, wherein each rate constant indicates a rate of transition from one of the four states to a different one of the four states for a component of a biological system for a constant value of an external factor;
   determining on a programmed processor, without numerical iteration over multiple time steps, a temporal change in a particular probability that the component is in a particular state of the four states after the initial time comprising determining three relaxation time constants that describe exponentially decreasing changes in probability with time based on the twelve rate constants; and
   determining the effect of the external factor on the biological system based on the temporal change in the particular probability that the component is in the particular state.

2. A method as recited in claim 1, wherein the component is a gated ion channel, the biological system is a membrane of a cell, and the external factor is at least one of an applied voltage and a concentration of a ligand.

3. A method as recited in claim 2, wherein
   the particular state is an open state; and
   said step of determining the effect of the external factor comprises determining temporal changes in an electrical current associated with a flow of ions through the ion channel based on the temporal change in the probability that the ion channel is in the open state.

4. A method as recited in claim 1, wherein the component is a protein, the biological system is a cell, and the external factor is a chemical compound.

5. A method as recited in claim 4, wherein the chemical compound is a member of a group comprising ligands, receptor agonists, receptor antagonists, antibodies and therapeutic agents.

6. A method as recited in claim 1, wherein:
   the method further comprises the step of determining four initial probabilities, each different initial probability indicating a probability that the component is in a different state of the four states at the initial time; and
   said step of determining the temporal change in the particular probability further comprises determining the particular probability based on the initial probabilities and the plurality of rate constants without numerical iteration over multiple time steps.

7. A method as recited in claim 1, said step of determining three relaxation time constants further comprising determining a first relaxation time constant designated by 1/a of the three relaxation time constants for the particular state using an equation that does not involve iterating time differentials over multiple time steps and that is equivalent to the following series of equations:

$$K1 = k12 + k10 + k13 + k21;$$

$$K2 = k01 - k21;$$

$$K3 = k31 - k21;$$

$$K4 = k21;$$

$$K5 = k01 + k02 + k03 + k20;$$

$$K6 = k10 - k20;$$

$$K7 = k30 - k20;$$

$$K8 = k20;$$

$$K9 = k32 + k31 + k30 + k23;$$

$$K10 = k13 - k23;$$

$$K11 = k03 - k23;$$

$$K12 = k23;$$

$$\alpha = K1 + K5 + K9;$$

$$\beta = K1*K9 + K1*K5 + K5*K9 - (K2*K6 + K3*K10 + K7*K11);$$

$$\gamma = K1*K5*K9 - (K1*K7*K11 + K2*K6*K9 + K2*K7*K10 + K3*K6*K11 + K3*K5*K10);$$

$$\delta = K3*K8*K10 - (K1*K7*K12 + K1*K8*K9 + K4*K7*K10 + K4*K6*K9 + K3*K6*K12);$$

$$A = \beta - (\alpha^2/3);$$

$$B = -1/27(2\alpha^3 - 9\alpha*\beta + 27\gamma);$$

$$\theta = \sqrt[3]{[-B/2 + \sqrt{(B^2/4 + A^3/27)}]};$$

$$\phi = \sqrt[3]{[-B/2 - \sqrt{(B^2/4 + A^3/27)}]}; \text{ and}$$

$$a = \alpha/3 + (\theta + \phi),$$

wherein
the plurality of rate constants are designated by "k" followed by a first numeral indicating a source state and a second numeral indicating a destination state for a transition of states associated with the rate constant and the four states are designated by numerals 0, 1, 2, 3, and the particular state is indicated by the numeral 0, and
an asterisk indicates multiplication, √ indicates a square root and $\sqrt[3]{}$ indicates a cube root.

8. A method as recited in claim 7, said step of determining three relaxation time constants further comprises determining a second relaxation time constant designated by 1/b of the three relaxation time constants for the particular state using an equation that does not involve iterating time differentials over multiple time steps and that is equivalent to:

$$b = \alpha/3 - [(\theta + \phi)/2 + ((\theta - \phi)/2)*\sqrt{(-3)}].$$

9. A method as recited in claim 8, said step of determining three relaxation time constants further comprises determining a third relaxation time constant designated by 1/c of the three relaxation time constants for a portion of the population in the first state (state 0) using an equation that does not involve iterating time differentials over multiple time steps and that is equivalent to:

$$c = \alpha/3 - [(\theta + \phi)/2 - ((\theta - \phi)/2)*\sqrt{(-3)}].$$

10. A method as recited in claim 9, said step of determining the temporal change in the particular probability further comprises determining at least one of the probabilities that the component is in the four states at steady state when temporal changes are negligible, designated $P0\infty$, $P1\infty$, $P2\infty$, $P3\infty$ for states 0, 1, 2, 3, respectively, using an equation that does not involve iterating time differentials over multiple time steps and that is equivalent to at least one of the following series of equations:

$$P0\infty = (K1*K7*K12 + K1*K8*K9 + K4*K7*K10 + K4*K6*K9 + K3*K6*K12 - K3*K8*K10)/\gamma;$$

$$P1\infty = (K2*K7*K12 + K3*K5*K12 + K2*K8*K9 + K4*K5*K9 + K3*K8*K11 - K4*K7*K11)/\gamma;$$

$$P3\infty = (K1*K8*K11 + K1*K5*K12 + K2*K8*K10 + K4*K5*K10 + K4*K6*K11 - K2*K6*K12)/\gamma; \text{ and}$$

$$P2\infty = 1 - P0\infty - P1\infty - P3\infty.$$

11. A method as recited in claim 10, wherein:
the method further comprises the step of determining four initial probabilities, each different initial probability indicating a probability that the component is in a different state of the four states at the initial time, designated P0i, P1i, P2i, P3i, for states 0, 1, 2, 3, respectively; and
said step of determining the temporal change in the particular probability further comprises determining the particular probability at time t, designated P0(t), based on the initial probabilities and the plurality of rate constants without numerical iteration over multiple time steps.

12. A method as recited in claim 11, said step of determining P0(t) further comprising determining the rates of temporal change for at least some of the four states at the initial time, designated P0i', P1i', P2i', P3i' for states 0, 1, 2, 3, respectively, using equations that do not involve iterating time differentials over multiple time steps and that are equivalent to the following series of equations:

$$P0i' = -K5*P0i + K6*P1i + K7*P3i + K8;$$

$$P1i' = -K1*P1i + K2*P0i + K3*P3i + K4; \text{ and}$$

$$P3i' = -K9*P3i + K10*P1i + K11*P0i + K12.$$

13. A method as recited in claim 12, said step of determining P0(t) further comprising determining the rate of temporal curvature of the particular probability for the particular state at the initial time, designated P0i", using equations that do not involve iterating time differentials over multiple time steps and that are equivalent to the following equation:

$$P0i'' = -K5*P0i' + K6*P1i' + K7*P3i'.$$

14. A method as recited in claim 13, said step of determining P0(t) further comprising using equations that do not involve iterating time differentials over multiple time steps and that are equivalent to the following equation:

$$Ca = [P0i'' + (b+c)*P0i' + b*c*(P0i - P0\infty)]/[(a-c)*(b-a)];$$

$$Cb = [P0i'' + (a+c)*P0i' + a*c*(P0i - P0\infty)]/[(c-b)*(b-a)];$$

$$Cc = [P0i'' + (a+b)*P0i' + a*b*(P0i - P0\infty)] / [(c-b)*(a-c)]; \text{ and}$$

$$P0(t) = P0\infty - Ca*e^{-at} - Cb*e^{-bt} - Cc*e^{-ct},$$

wherein e is a base for natural logarithms.

15. A non-transitory computer readable medium carrying one or more sequences of instructions for determining an effect of an external factor on a biological system by analyzing a given component of the biological system, wherein the given component occupies only one of four possible states, and wherein execution of the one or more sequences of instructions by one or more processors causes the one or more processors to perform the steps of:

receiving, for a particular time interval starting at an initial time, twelve non-degenerate and non-zero rate constants, wherein each rate constant indicates a rate of transition from one of the four states to a different one of the four states for a component of a biological system in presence of an external factor;

determining a temporal change in a particular probability that the component is in a particular state of the four states after the initial time comprising determining three relaxation time constants that describe exponentially decreasing changes in probability with time based on the twelve rate constants without numerical iteration over multiple time steps;

determining the effect of the external factor on the biological system based on the temporal change in the particular probability that the component is in the particular state; and presenting data that indicates at least one of the effect of the external factor and the temporal change in the particular probability.

16. An apparatus for determining an effect of an external factor on a biological system by analyzing a given component of the biological system, wherein the given component occupies only one of four possible states, comprising;

a processor;

a computer-readable medium; and one or more sequences of instructions stored on the computer-readable medium, wherein execution of the one or more sequences of instructions by the processor causes the processor to perform the steps of:

receiving, for a particular time interval starting at an initial time, twelve non-degenerate and non-zero rate constants, wherein each rate constant indicates a rate of transition from one of the four states to a different one of the four states for a component of a biological system in presence of an external factor;

determining a temporal change in a particular probability that the component is in a particular state of the four states after the initial time comprising determining three relaxation time constants that describe exponentially decreasing changes in probability with time based on the twelve rate constants without numerical iteration over multiple time steps;

determining the effect of the external factor on the biological system based on the temporal change in the particular probability that the component is in the particular state; and presenting data that indicates at least one of the effect of the external factor and the temporal change in the particular probability.

17. A method for determining an effect of an external factor on a system by analyzing a given component of the system, wherein the given component occupies only one of four possible states, comprising the steps of:

determining, for a particular time interval starting at an initial time, twelve non-degenerate and non-zero rate constants, wherein each rate constant indicates a rate of transition from one of the four states to a different one of the four states for a component of a system for a constant value of an external factor;

determining on a programmed processor, without numerical iteration over multiple time steps, a temporal change in a particular probability that the component is in a particular state of the four states after the initial time comprising determining three relaxation time constants that describe exponentially decreasing changes in probability with time based on twelve of rate constants; and determining the effect of the external factor on the system based on the temporal change in the particular probability that the component is in the particular state.

18. A method for determining a given component based on an effect of an external factor on a system by analyzing the given component of the system, wherein the given component occupies only one of four possible states, comprising the steps of:

determining a time history of an effect of an external factor on a system with a component that occupies one of the four states;

determining on a programmed processor, without numerical iteration over multiple time steps, three relaxation time constants that describe exponentially decreasing changes in probability with time based on the time history of the effect of the external factor; and determining, twelve non-degenerate and non-zero rate constants for a transition from one state of the four states to a another state of the four states, without numerical iteration over multiple time steps, based on the three relaxation time constants.

\* \* \* \* \*

UNITED STATES PATENT AND TRADEMARK OFFICE
CERTIFICATE OF CORRECTION

| | |
|---|---|
| PATENT NO. | : 7,881,877 B2 |
| APPLICATION NO. | : 11/687635 |
| DATED | : February 1, 2011 |
| INVENTOR(S) | : Goldman |

It is certified that error appears in the above-identified patent and that said Letters Patent is hereby corrected as shown below:

Column 9, line 3 (Equation 18), remove "$\sqrt{}$" (leave exponent "3");

Column 9, line 62 (Equation 25), replace "$k9$" with "$K9$";

Column 9, line 62 (Equation 26), replace "$k1$" with "$K1$".

Signed and Sealed this
Nineteenth Day of April, 2011

David J. Kappos
*Director of the United States Patent and Trademark Office*